United States Patent
Kern

(10) Patent No.: US 10,046,160 B1
(45) Date of Patent: Aug. 14, 2018

(54) ELECTRONIC SKIN TREATMENT DEVICE AND METHOD

(71) Applicant: Nu Skin Enterprises, Inc., Provo, UT (US)

(72) Inventor: Dale G. Kern, Hyde Park, UT (US)

(73) Assignee: NSE Products, Inc., Provo, UT (US)

( * ) Notice: Subject to any disclaimer, the term of this patent is extended or adjusted under 35 U.S.C. 154(b) by 0 days.

(21) Appl. No.: 13/630,513

(22) Filed: Sep. 28, 2012

Related U.S. Application Data

(60) Provisional application No. 61/541,860, filed on Sep. 30, 2011.

(51) Int. Cl.
*A61N 1/36* (2006.01)
*A61N 7/00* (2006.01)
*A61N 1/18* (2006.01)
*A61N 1/32* (2006.01)

(52) U.S. Cl.
CPC .............. *A61N 1/328* (2013.01); *A61N 1/18* (2013.01); *A61N 7/00* (2013.01)

(58) Field of Classification Search
CPC ................. A61N 1/36021; A61N 7/00; A61N 2007/0004; A61N 2007/0008; A61N 2007/0034; A61N 2007/0073
USPC .............................................. 607/50, 72, 115
See application file for complete search history.

(56) References Cited

U.S. PATENT DOCUMENTS

| | | | |
|---|---|---|---|
| 3,320,947 A * | 5/1967 | Knoll | 600/554 |
| 4,846,181 A * | 7/1989 | Miller | A61N 1/326 607/50 |
| 5,016,616 A | 5/1991 | Hu | |
| 5,147,297 A | 9/1992 | Myers et al. | |
| 5,162,043 A | 11/1992 | Lew et al. | |
| 5,298,017 A | 3/1994 | Theeuwes et al. | |
| 5,326,341 A | 7/1994 | Lew et al. | |
| 5,405,317 A | 4/1995 | Myers et al. | |
| 5,441,613 A | 8/1995 | McCormick et al. | |
| 5,685,837 A | 11/1997 | Horstmann | |
| 6,119,038 A | 9/2000 | Cook | |
| 6,421,561 B1 | 7/2002 | Morris | |
| 6,584,349 B1 | 6/2003 | Sage, Jr. et al. | |
| 6,653,014 B2 | 11/2003 | Anderson et al. | |
| 7,850,997 B2 | 12/2010 | Romero et al. | |
| 7,959,951 B2 | 6/2011 | Stefano et al. | |

(Continued)

OTHER PUBLICATIONS

M. Rossi et al., "Spectral analysis of skin laser Doppler blood perfusion signal during cutaneous hyperemia in response to acetylcholine iontophoresis and ischemia in normal subjects," Clinical Hemorheology and Microcirculation 31(4):303-10 (2004). Abstract Only.

(Continued)

*Primary Examiner* — Michael D Abreu
(74) *Attorney, Agent, or Firm* — Dorsey & Whitney LLP

(57) ABSTRACT

Disclosed is a method for treating dermis and hypodermis by placing at least a first electrode at the surface of a to-be-treated skin region and contacting a second electrode at another position on the body to be treated then applying between the electrodes a current with pulse component, said current being sufficient to produce electro-osmotic pressure/velocity wavefronts corresponding to the fundamental frequency in blood vessels in the dermis and hypodermis of the skin region.

13 Claims, 11 Drawing Sheets

(56) References Cited

U.S. PATENT DOCUMENTS

| | | | | |
|---|---|---|---|---|
| 2003/0004556 | A1* | 1/2003 | McDaniel | A61K 8/494 607/88 |
| 2003/0032900 | A1* | 2/2003 | Ella | A61H 7/008 601/6 |
| 2007/0185431 | A1 | 8/2007 | Kern | |
| 2010/0042018 | A1* | 2/2010 | Kleinsinger | A61H 9/0057 601/2 |
| 2010/0049180 | A1* | 2/2010 | Wells | A61N 5/0616 606/12 |
| 2010/0305206 | A9 | 12/2010 | Messadek | |
| 2011/0015687 | A1* | 1/2011 | Nebrigic et al. | 607/3 |
| 2011/0028548 | A1 | 2/2011 | Fossel | |
| 2011/0118655 | A1 | 5/2011 | Fassih et al. | |
| 2013/0289416 | A1* | 10/2013 | Feferberg | A61N 1/0468 600/476 |

OTHER PUBLICATIONS

Ackaert et al. "Mechanistic studies of the transdermal iontophoretic delivery of 5-OH-DPAT in vitro" J. Pharm. Sci. Jan. 2010;99(1):275-85. Abstract Only.

Adams et al. "Microcirculatory and therapeutic effects of whole body periodic acceleration (pGz) applied after cardiac arrest in pigs" Resuscitation. Mar. 8, 2011 [Epub] Abstract Only.

Aramaki et al. "Intradermal Delivery of Antisense Oligonucleotides by the Pulse Depolarization Iontophretic System" Bio. Pharm. Bull. 26(10)1461-1466 (2003).

Arashi et al. "Vibration therapy accelerates healing of Stage I pressure ulcers in older adult patients" Adv. Skin Wound Care. Jul. 2010;23(7):321-7 Abstract Only.

Baky et al. "Nitric oxide pros and cons: The role of 1-arginine, a nitric oxide precursor, and idebenone, a coenzyme-Q analogue in ameliorating cerebral hypoxia in rat" Brain Res. Bull. Jul. 15, 2010 [Epub] Abstract Only.

Bayrakci et al. "Effects of mechanical massage, manual lymphatic drainage and connective tissue manipulation techniques on fat mass in women with cellulite" J. Eur. Acad. Dermatol. Vereneol. Feb. 2010;24(2):138-42. Epub Jul. 13, 2009 Abstract Only.

Bucci et al. "Hydrogen sulphide in heart and systemic circulation" Inflamm Allergy Drug Targets. Apr. 1, 2011; 10(2):103-8. Abstract Only.

Brooks et al. Measurement of Exhaled Nitric Oxide in a General Population Sample: A comparison of the Medisoft HypAir Fe(No) and Aerocrine NIOX Analyzers J. Asthma Mar. 9, 2011 [Epub] Abstract Only.

Button et al. "The effect of multidirectional mechanical vibration on peripheral circulation of humans" Clin Physiol Funct Imaging Jul. 2007;27(4):211-6.

Calcagni et al. "Microvascular Response to shock Wave Application in Striated Skin Muscle" J. Surg. Res. Jan. 5, 2010 Epub. Abstract Only.

Casey et al. "Nitric oxide-mediated vasodilation becomes independent of {beta}-adrenergic receptor activation with increased intensity of hypoxic exercise" J. Appl. Physiol., Mar. 2011; 110(3):687-94. Epub Dec. 30, 2010 Abstract Only.

Charkoudian N. "Mechanisms and Modifiers of reflex induced cutaneous vasodilation and vasoconstriction in humans" J. Appl. Physiol. May 6, 2010. Abstract Only.

Chen et al. S-glutathionylation uncouples eNOS and regulates its cellular and vascular function Nature Dec. 23, 2010;468(7327):1115-8. Abstract Only.

Cheriyan et al. "Inhibition of p38 mitogen-activated protein kinase improves nitric oxide-mediated vasodilatation and reduces inflammation in hypercholesterolemia" Circulation. Feb. 8, 2011;123(5):515-23. Epub Jan. 24, 2011. Abstract Only.

Droog et al. "Nonspecific vasodilatation during transdermal iontophoresis—the effect of voltage over the skin" Microvascular Research 65 (2003) 172-178.

Dubey et al. "Electrically-assisted delivery of an anionic protein across intact skin: Cathodal iontophoresis of biologically active ribonuclease T1" J. Control Release. Mar. 21, 2011 [Epub] Abstract Only.

Durand et al. "Vasodilatation in response to repeated anodal current application in the human skin relies on aspirin-sensitive mechanisms" J. of Physiology (2002) 540.1 pp. 261-269.

Eby GA Strong humming for one hour daily to terminate chronic rhinosinusitis in four days: a case report and hypothesis for action by stimulation of endogenous nasal nitric oxide production Med Hypotheses 2006;66(4):851-4. Epub Jan. 10, 2006. Abstract Only.

Emanuele et al. "A multilocus candidate approach identified ACE and HIF1A as susceptibility genes for cellulite" J Eur Acad Dermatol Venereol. Aug. 2010;24(8):930-5. doi: 10.1111/j.1468-3083.2009.03556.x. Epub Jan 6, 2010.

Gazelius, Bertil "Iontophoresis—Theory" Innovations in Microvascular Diagnosis. Perimed Periflux Systems Perilont Marketing Materials. 8 pages.

Gielen et al. Exercise-induced Modulation of Endothelial Nitric Oxide Production. Curr Pharm Biotechnol. Jan. 11, 2011 [Epub] Abstract Only.

Granqvist et al. "Paranasal sinus ventilation by humming" J. Acoust. Soc. Am. May 2006;119(5 Pt 1):2611-7. Abstract Only.

Grossman et al. "The Effect of Iontophoresis on the Cutaneous Vasculature: Evidence for Current-Induced Hyperemia" Microvascular Research 50, 444-452 (1995) pp. 444-452.

Heller A. "Electrochemistry and nitric oxide mass transport in cancer: why ingestion of sodium nitrite could be effective in treating vascularized tumors" Phys. Chem. Chem. Phys. Sep. 14, 2010;12(34):9972-5 Epub Jun. 11, 2010.

Hikima et al. Mechanisms of Synergistic Skin Penetration by Sonophoresis and Iontophoresis Biol. Pharm. Bull. 32(5) 905-909 (2009).

Ikeyama et al. "Neuronal nitric oxide synthase in epidermis is involved in cutaneous circulatory response to mechanical stimulation" J. Invest Dermatol. Apr. 2010; 130(4):1158-66. Epub Nov. 26, 2009. Abstract Only.

Jobgen et al. "Regulatory role for the arginine-nitric oxide pathway in metabolism of energy substrates" J. Nutr. Biochem. Sep. 2006; 17(9):571-88. Epub Jan. 9, 2006. Abstract Only.

Johnson et al. "Local thermal control of the human cutaneous circulation" J. Appl. Physiol. Jun. 3, 2010. Epub. Abstract Only.

Kerschan-Schindl et al. "Whole-body vibration exercise leads to alterations in muscle blood volume" Clinical Physiology 21, 3, 377-382.

Kahn et al. Treatment of cellulite Part I. Pathophysiology: J. Am. Acad. Dermatol. vol. 62, No. 3 p. 361-370.

Kahn et al. Treatment of cellulite Part II. Advances and controversies: J. Am. Acad. Dermatol. vol. 62, No. 3 p. 373-382.

Knobloch et al. Cellulite and extracorporeal Shockwave therapy (CelluShock-2009)—a Randomized Trial BMC Women's Health 2010, 10:29 http://www.biomedcentral.com/1472-6874/10/29.

Kulick MI. "Evaluation of a noninvasive, dual-wavelength laser-suction and massage device for the regional treatment of cellulite" Plast Reconstr Surg. Jun. 2010; 125(6):1788-96. Abstract Only.

Kvandal et al. Regulation of human cutaneous circulation evaluated by laser Doppler flowmetry, iontophoresis, and spectral analysis: importance of nitric oxide and prostaglandines. Microvasc. Res. May 2003 65(3): 160-171. Abstract Only.

Lin et al. Effects of local vibration on the levels of plasma endothelin and nitric oxide in rabbits Wei Sheng Yan Jiu Jan. 30, 2000;29(1):10-1 Abstract Only.

Lohman et al. "The effect of whole body vibration on lower extremity skin blood flow in normal subjects" Med Sci. Monit Feb. 2007; 13(2):CR71-6. Abstract Only.

Lythgo et al. "Whole-body vibration dosage alters leg blood flow." Clin. Physiol Funct. Imaging. Jan. 2009; 29(1):53-9. Abstract Only.

Maloney-Hinds et al. "The effect of 30 Hz vs. 50 Hz passive vibration and duration of vibration on skin blood flow in the arm" Med Sci Monit, 2008; 14(3): CR112-116.

(56) References Cited

OTHER PUBLICATIONS

Maloney-Hinds et al. "The Role of Nitric Oxide in Skin Blood Flow Increases Due to Vibration in Healthy Adults and Adults with Type 2 Diabetes" Diabetes Technology & Therapeutics vol. 11(1) 2009 39-43.
Marszaleck "Skin circulation—measurements with laser-doppler" Med Pr. 1996;47(4):411-8. Abstract Only.
Mattar EH Effect of age on the biomechanical and microcirculatory properties of the skin in healthy individuals and during venous ulceration Indian J. Dermatol. Jan. 2011 56(1):19-24. Abstract Only.
Moor Instruments Product Sheet. Tissue blood flow and temperature monitoring with moorVMS-LDF™ 4 pages.
Müller et al. "ACE inhibition promotes upregulation of endotheilial progenitor cells and neoangiogensis in cardiac pressure overload" Cardiovasc Res Jul. 1, 2009;83(1):106-14 Epub Apr. 20, 2009 Abstract Only.
Nakagami et al. Effect of vibration on skin blood flow in an in vivo microcirculatory model: BioScience Trends 2007;1(3):161-166.
Oh et al. "Effect of sub-sonic vibration on the proliferation and maturation of 3T3-L1 cells" Life Sciences 88 (2011) 169-177.
Petrofsky et al. "Effects of electrical stimulation on skin blood flow in controls and in and around stage III and IV wounds in hairy and nonhairy skin" 2005, vol. 11, No. 7 CR209-CR316. Abstract Only.
Piantadosi, CA. "Regulation of Mitochondrial Processes by Protein S-Nitrosylation" Mar. 10, 2011. Epub. Abstract Only.
Pikal et al. Study of the mechanisms of flux enhancement through hairless mouse skin by pulsed DC iontophoresis Pharm Res. Mar. 1991;8(3):365-9. Abstract Only.
Potera, Carol. Aug 1, 2010 Genetic Engineering & Biotechnology News "Nanoparticles Deliver Nitric Oxide Locally" vol. 30, No. 14 3 pages.
Poyton, Robert O. "Therapeutic Photobiomodultion: Nitric Oxide and a Novel Function of Mitochondrial Cytochrome C Oxidase" Discov Med. 11(57):154-9 Feb. 2011.
Pullamsetti et al. "cAMP Phosphodiesterase Inhibitors Increases Nitric Oxide Production by Modulating Dimethylarginine Dimethylaminohydrolases" Circulation Mar. 7, 2011 [Epub] Abstract Only.
Raiman et al. Drug adsorption in human skin: a streaming potential study J. Pharm. Sci. Dec. 2003; 92(12):2366-72. Abstract Only.
Reich et al. "Electrical Stimulation of Skin" Jul.-Aug. 1990 vol. 29, No. 6 p. 395.
Rosenfeld et al. "Nitric oxide synthase forms N—NO-pterin and S—NO-Cys: Implications for activity, allostery, and regulation" published Jul. 21, 2010 as Manuscript M109.072496 at http://www.jbc.org/cgi/doi/10.1074/jbc.M109/072496 pp. 1-20.
Santamaria et al. "Nasal nitric oxide assessment in primary ciliary dyskinesia using aspiration, exhalation, and humming" Med Sci. Monit. Feb. 2008; 14(2):CR80-85. Abstract Only.
Sammeta et al. Transdermal drug delivery enhanced by low voltage electropulsation (LVE) Pharm. Dev. Technol. 2009;14(2):159-64. Abstract Only.
Schuetz et al. "Effect of amino acid sequence on transdermal iontophoretic peptide delivery" Eur J. Pharm. Sci. Dec. 2005;26(5):429-37. Epub Sep. 6, 2005. Abstract Only.
Schuetz et al. "Transdermal iontophoretic delivery of triptorelin in vitro" J. Pharm. Sci. Oct. 2005; 94(1):2581-82.
Sebastiani et al. "Effect of lactic acid and iontophoresis on drug permeation across rabbit ear skin" Int. J. Pharm. Mar. 23, 2005;292(1-2):119-26. Abstract Only.
Sumano et al. "Use of Electrical Stimulation for Wound Healing in Dogs" vol. 57(2) 2002 9 pgs.
Sylvestre et al. "In Vitro optimization of dexamethasone phosphate delivery by iontophoresis" Phys Ther. Oct. 2008;88(10)1177-85. Epub Aug. 21, 2008. Abstract Only.
Taveira et al. "Effect of the iontophoresis of a chitosan gel on doxorubicin skin penetration and cytotoxicity" J. Control Release Feb. 20, 2009;134(1):35-40. Epub Nov. 12, 2008.
Tew et al. Effects of ageing and fitness on skin-microvessel vasodilator function in humans Eur. J. Appl. Physiol. May 2010;109(2):173-81. Epub Jan. 5, 2010.
Toda et al. Alteration of nitric oxide-mediated blood flow regulation in diabetes mellitus Pharmcol Ther. Sep. 2010; 127(3):189-209. Epub May 28, 2010.
Vanin et al. "Autowave distribution of nitric oxide and its endogenous derivates in biosystems strongly enhances their biological effects: A working hypothesis" Nitric Oxide. Jul. 13, 2010 Epub.
Veber et al. "Wavelet analysis of blood flow dynamics: effect on the individual oscillatory components of iontophoresis with pharmacologically neutral electrolytes" Phys. Med. Biol. 49 (2004) pp. N111-N117.
Wang et al. Oxidized low-density lipoprotein inhibits nitric-oxide-mediated coronary arteriolar dilation by up-regulating endothelial arginase I. Abstract Only.
Weitzberg et al. Humming greatly increases nasal nitric oxide Am. J Respir. Crit. Care Med. Jul. 15, 2002;166(2):144-5. Abstract Only.
Wolchok et al. The effect of bioreactor induced vibrational stimulation on extracellular matrix production from human derived fibroblasts Biomaterials. Jan. 2009;30(3):327-35 Epub Oct. 19, 2008. Abstract Only.
Yan et al. "Evaluation of constant current alternating current iontophoresis for transdermal drug delivery" J. Control Release Dec. 10, 2005;110(1):141-50 Epub Nov. 9, 2005. Abstract Only.
Yang et al. "Electroosmotic Flow in Microchannels" J. of Colloid and Interface Science 239, 98-105 (2001) pp. 98-105.
Yohannes et al. "Non-invasive low frequency vibration as a potential emergency adjunctive treatment for heart attack and stroke. An in vitro flow model" J. Thromb. Thrombolysis Jun. 2008;25(3):251-8 Epub May 30, 2007. Abstract Only.
Zheng et al. "Effects of a low-frequency sound wave therapy programme on functional capacity, blood circulation and bone metabolism in frail old men and women" Clin. Rehabil. Oct. 2009;23(10)897-908 Epub Aug. 28, 2009.
FDA Executive Summary: Petitions to Request Change in Classification for Cranial Electrotherapy Stimulators. Feb. 10, 2012, Neurologic Devices Panel Meeting. 83 pages.

\* cited by examiner

TABLE 1: SUMMARY BIOINSTRUMENTATION AND IMAGING DATA RESULTS

| PARAMETER | TREATMENT | TIME POINT | N | MEAN | SD | MINIMUM | MAXIMUM |
|---|---|---|---|---|---|---|---|
| LASER DOPPLER | ageLOC BODY SHAPING GEL | BASELINE | 10 | 368.16 | 40.25 | 282.37 | 410.63 |
| | | POST-APPLICATION | 10 | 538.21 | 76.26 | 408.47 | 638.13 |
| | GALVANIC PRE-TREATMENT GEL | BASELINE | 10 | 373.92 | 75.80 | 256.03 | 538.03 |
| | | POST-APPLICATION | 10 | 513.64 | 76.84 | 338.23 | 610.43 |
| CHROMA METER $a^*$ | ageLOC BODY SHAPING GEL | BASELINE | 10 | 7.79 | 2.17 | 4.58 | 12.35 |
| | | POST-APPLICATION | 10 | 8.14 | 1.92 | 5.91 | 12.56 |
| | GALVANIC PRE-TREATMENT GEL | BASELINE | 10 | 8.14 | 1.69 | 4.50 | 9.89 |
| | | POST-APPLICATION | 10 | 8.51 | 1.75 | 6.17 | 11.86 |

FIG. 13

TABLE 2: CHANGE FROM BASELINE BIOINSTRUMENTATION AND IMAGING DATA RESULTS

| PARAMETER | TIME POINT | p-VALUE a | TREATMENT | SUBJECTS IMPROVED, % | SUBJECTS WORSENED, % | MEAN CHANGE | MEAN CHANGE, % | p-VALUE b |
|---|---|---|---|---|---|---|---|---|
| LASER DOPPLER | POST-APPLICATION | 0.231 | GALVANIC PRE-TREATMENT GEL | 100.0 | 0.0 | 139.72 | 37.4 | <0.001 |
| | | | ageLOC BODY SHAPING GEL | 100.0 | 0.0 | 170.05 | 46.2 | <0.001 |
| CHROMA METER $a^*$ | POST-APPLICATION | 0.963 | GALVANIC PRE-TREATMENT GEL | 40.0 | 60.0 | 0.37 | 4.6 | 0.574 |
| | | | ageLOC BODY SHAPING GEL | 60.0 | 40.0 | 0.35 | 4.4 | 0.247 | a BETWEEN TREATMENT COMPARISONS USING PAIRED t-TEST
b WITHIN TREATMENT COMPARISONS WITH BASELINE USING t-TEST

FIG. 14

ELECTRONIC SKIN TREATMENT DEVICE AND METHOD

TECHNICAL FIELD

The present disclosure relates generally to the field of skin treatment devices. More particularly, the present disclosure relates to an electronic skin treatment device configured to improve blood circulation in the skin, in particular for alleviating skin disorders such as cellulite.

BACKGROUND

A variety of galvanic skin treatment devices are known in the art. See, e.g., U.S. Pat. Nos. 5,147,297, 5,162,043, 5,298,017, 5,326,341, 5,405,317, 5,685,837, 6,584,349, 6,421,561 and 6,653,014, and U.S. Pat. App. Publication No. 2007/0185431. Galvanic skin treatment devices may include, among other things, an electrode pair brought into contact with a patient, each end of the electrode being electrically connected to either the anode or the cathode of a current supply from a power delivery circuit operably connected to a control circuit for the electrical instrument. Power for the device is usually provided by DC batteries that, when providing power to the circuitry, allow application of a voltage to the electrodes to create a regulated current flow in the skin.

An anode and a cathode electrode may function as a galvanic couple, comprising a donor electrode and a counter electrode. Such a combination produces an electric potential across the skin when brought in contact or close proximity thereto, and provides a current flow when body tissue and/or fluids form a complete circuit between the electrodes.

A use known in the art for such galvanic skin treatment devices, as exemplified in the references cited above, is iontophoresis. Iontophoresis is essentially an ion delivery method, wherein ions bearing positive and negative charges may be driven across the skin at the sites of electrical nodes. Typically, the patient applies a pharmacologically active topical agent to the skin, such as a cream, spray, or lotion, which contains pharmacologically active ions. The application of direct current to the skin, using the galvanic device, then drives the ions into the skin, where they are absorbed by the body and react therein to produce the desired biological effect.

Some iontophoretic applications have been indicated for the prevention or treatment of ischemia, or poor blood circulation. Ischemia is the result of an inadequate flow of blood to a part of the body, which in some cases may be caused by constriction or blockage of the blood vessels supplying it. In severe cases, ischemia can result in tissue damage because of a lack of oxygen and nutrients. In less severe cases, ischemia can result in the build-up of metabolic wastes in the tissue, which can, over time, lead to increased fat deposits, increased concentration of toxicity (i.e., toxic metabolic by-products or environmental toxins) in the tissue, and decreased metabolic activity, among other things.

Where iontophoresis is used to prevent or treat ischemia, the topical application may include one or more natural compounds such as terpenoids, one or more synthetic amino acids such as L-arginine, or one or more synthetic pharmacological agents such as acetylcholine. A significant amount of research has been done in this field, and its methods are well known in the art. See, e.g., M. Rossie et al., "Spectral analysis of skin laser Doppler blood perfusion signal during cutaneous hyperemia in response to acetylcholine iontophoresis and ischemia in normal subjects," Clinical Hemorheology and Microcirculation 31:303-10 (2004).

Other, non-pharmacological methods are also known in the art for the treatment and prevention of ischemia. For example, it was reported by Kerschan-Schindl et al. (Clinical Physiology 21(3), 377-382 (2001)) that physical vibration applied to the body can lead to increased blood flow volume. In this study, the subjects were exposed to whole-body vibration. Localized, externally introduced vibration, through devices used in massage is also known as a treatment for various conditions. Massage is claimed to improve blood circulation, to flush lactic acid from the muscles and to improve the circulation of the lymph fluid which carries metabolic waste away from muscles and internal organs, resulting in lower blood pressure and improved body function.

Recently, research has recognized that low blood flow is associated with tissue considered to exhibit cellulite, a condition of skin for which treatment is often sought. See "A multilocus candidate approach identifies ACE and HIF1A as susceptibility genes for cellulite", 24 Journal of European Academy of Dermatology and Venerology 935-50 (2010). It is not clear whether the low blood flow is a cause or an effect of cellulite (or both). However, this finding suggests that increasing blood flow may help address this condition.

What is needed in the art is an improved system and method for increasing blood flow in targeted skin regions of the body.

SUMMARY

In one embodiment, disclosed herein is a method for treating dermis and hypodermis layers comprising placing at least a first electrode at the surface of a to-be-treated skin region and contacting a second electrode at another position on the body to be treated; and applying between the electrodes a current with pulse component, said current being sufficient to produce electro-osmotic pressure/velocity wavefronts corresponding to the fundamental frequency in blood vessels in the skin.

In another embodiment, disclosed herein is a device for treating dermis and hypodermis layers: a first electrode for placement at a to be treated skin surface; and means for delivering a pulsing current from the first electrode into skin, said current being sufficient to produce electro-osmotic pressure/velocity wavefronts in blood vessels in the skin.

While multiple embodiments are disclosed, still other embodiments in accordance with the present disclosure will become apparent to those skilled in the art from the following detailed description, which shows and describes illustrative embodiments. As will be realized, the disclosed embodiments are capable of modifications in various aspects, all without departing from the spirit and scope of thereof. Accordingly, the drawings and detailed description are to be regarded as illustrative in nature and not restrictive.

DESCRIPTION OF THE FIGURES

While the specification concludes with claims particularly pointing out and distinctly claiming the subject matter that is regarded as forming the various embodiments of the present disclosure, it is believed that the embodiments will be better understood from the accompanying figures, in which:

FIGS. 13 and 14 are tables showing numerical results for testing as described in Example 1, set forth below.

DETAILED DESCRIPTION

The present disclosure provides an electronic skin treatment device for the improvement of blood flow within the skin. In one embodiment, the device is adapted for and appropriate for self-application. In one embodiment the electronic skin treatment device has a first electrode that is brought into contact with the skin surface to be treated, with a second electrode that contacts a point displaced from the skin surface to be treated. The electrodes may be at the end of wires running to a current source. In one embodiment, the first and second electrodes are on different surfaces of a handheld unit, for self application. The user activates the device so as to generate and apply between the electrodes a varying current. A current flows through a portion of the body of the person treated positioned between the skin region to be treated and the hand of the person being treated. In other embodiments, one person can assist another in application of the device, and place first and second electrodes on the person to be treated, with one electrode on the skin to be treated and the other at a displaced location on the person to be treated. In still another embodiment, the skin treating surface has multiple anode-cathode pairs on a common surface. The varying current may take on many waveforms. In one embodiment, the current has generally the form of a square wave. In one embodiment, each cycle of the square wave may last between 1 and 100 milliseconds, resulting in a fundamental frequency of 10 to 1000 Hz for the electronic signal to which the tissue is exposed. The duration of the square wave is selected in part to provide a power level comfortable to the user.

Human tissue has a resistance that varies according to the type of tissues; thus the current in the tissue will generate voltage drops between various points. As explained in greater detail below, the voltage drop is sufficient to produce in at least some portion of some of the blood vessels of the skin region to be treated electro-osmotic pressure/velocity wavefronts corresponding to the fundamental frequency of the electronic signal generated in the device and fed to the electrodes. These electro-osmotic wavefronts produce a mechanical, vibratory-like action in the walls of blood vessels where they are produced.

Structure of Human Skin

Embodiments of the present disclosure are directed to the application of electrical current to the surface of human skin and penetration of the current into dermis and hypodermis of a skin region to be treated. As will be appreciated, a human skin region (including epidermis, dermis and hypodermis) is comprised of various layers, with dermis and hypodermis traversed by numerous blood vessels and capillaries. An applied electrical signal and field may be sufficient to extend into one or more of the various layers of the skin region to effect flow in the blood vessels and capillaries located therewithin.

Figure 1A:
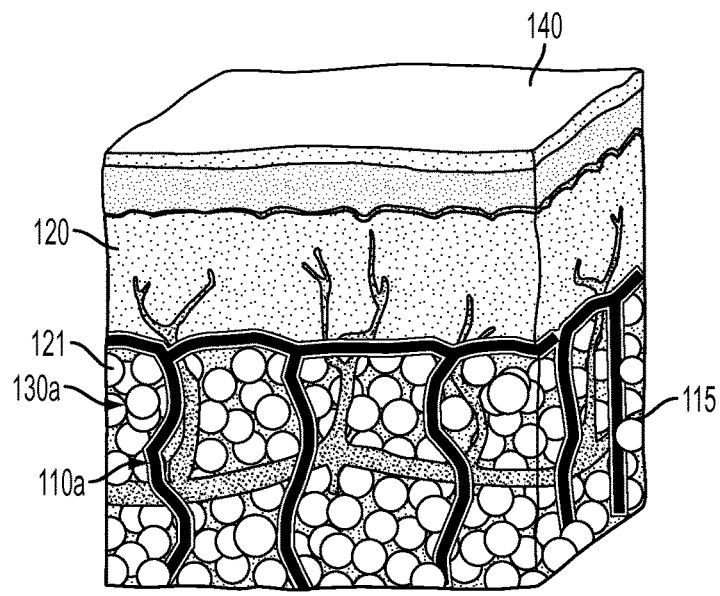
FIGS. 1a and 1b illustrate the various layers of human skin, and the vessels and capillaries that allow blood to flow therethrough, illustrating a non-cellulite condition in FIG. 1a and a cellulite condition in FIG. 1b.
Figure 1B:
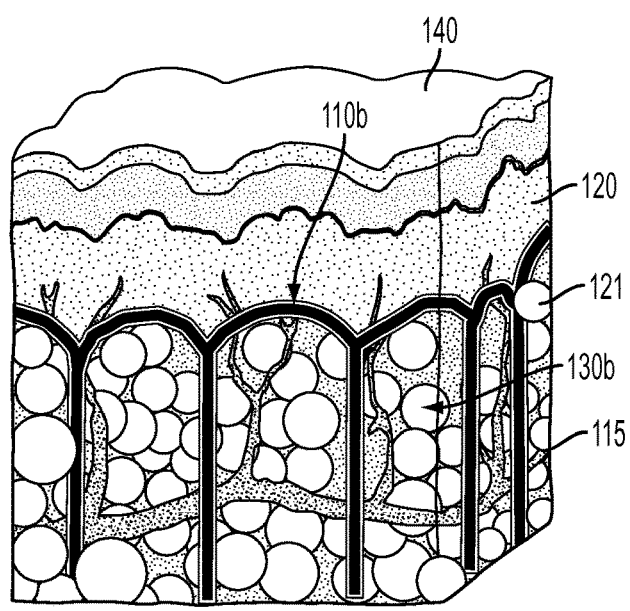

FIGS. 1a and 1b provide diagrams of human skin in an adult female, directed to the presence of cellulite in the layers thereof. Cellulite is a localized metabolic disorder of subcutaneous tissue that provokes an alteration of the female body shape. It presents as a modification of skin topography evident by skin dimpling and nodularity, and is caused by the herniation of subcutaneous fat within fibrous connective tissue. FIG. 1a depicts human skin of an adult female before a substantial amount of cellulite has been formed, whereas FIG. 1b depicts human skin of an adult female after the formation of cellulite. As shown therein, connective collagen bands (septae) 110a, 110b anchor the inner layer of the skin (the dermis 120) to the hypodermis 121 and muscle (not shown) below. These connective bands hold the skin that covers the body.

Cellulite tends to develop in the subcutaneous fatty layer 121 or hypodermis. This layer of fat is unique in its structure compared to the other layers, because fat globules 130a, 130b surround the strands of connective collagen bands 110a, 110b. Fat globules are lumps of fat cells. As fat globules grow or are added, the cells fill up and push the dermis 120 and epidermis 140 of the skin outwards. A dimpling effect is caused as a result of the fat globules pushing the outer skin layers outwards and the collagen connective bands becoming tensioned, restraining outer skin expansion at certain locations by anchoring that skin to the muscles. This is shown in FIGS. 1a and 1b by comparing band 110a to tensioned band 110b, and regular fat globules 130a to distending fat globules 130b. Blood vessels and capillaries 115 deliver lipids to the organs of the body for energy, and excess lipids are delivered to the fat globules 130a, 130b by the vessels and capillaries for storage therein. It is believed that poor circulation and inadequate blood flow in the region depicted in FIGS. 1a and 1b can lead to inefficient use of nutrients and an excess accumulation of lipids in the fat globules 130a, 130b, resulting over time in cellulite formation as depicted in FIG. 1b.

In contrast to the structure shown in FIGS. 1a and 1b, the collagen connective bands in men are less likely to be "vertical" (relative to the skin surface). They attach between the skin and the muscle at multiple angles. This results in fewer individual points where the collagen bands restrain skin that has undergone fat cell growth, such that the points of dimpling will occur. As shown in FIGS. 1a and 1b, women have more vertical bands (relative to the skin surface) that prevent the smooth expansion of all points in a skin area. The stored fat globules therefore produce a more prominent dimpling effect.

Thus, it is appreciated that the collagen connective bands 110a, 110b in women produce tissue regions that, when filled with fat globules 130a, 130b, begin to exhibit an uneven skin surface. As these fat cells grow, the fat protrudes outwards toward the epidermis 140 and dermis layer 120. The collagen bands restrain the expansion of the skin at their connection points, thus producing the dimpling effect on the outer surface 140 of the skin.

It will be further appreciated that the growth of fat globules 130a, 130b may restrict the flow of blood in the vessels and the capillaries of the skin. For example, as shown in FIG. 1b, the vessels and capillaries 115 extending upwardly through the subcutaneous layer or hypodermis 121 may be restricted, thus decreasing the blood flow therethrough. As discussed above, decreased blood flow with a related decrease in local metabolism may lead to an increased accumulation of fat and cellulite, which may in turn decrease blood flow even further. Thus, the accumulation of cellulite may result in a "negative feedback loop," where accumulation of cellulite causes increased accumulation of cellulite. Increasing blood flow through the vessels and capillaries 115 may help to prevent and reverse the excess accumulation of lipids in the globules 130a, 130b.

Given this understanding of the structure and effects of cellulite, the present device and method seek to improve blood flow in and around the tissue regions in which cellulite is observed. As explained next, the device and method seek to improve blood flow by a form of vibration. However, instead of introducing vibration from outside the body and using this in a gross mechanical manipulation of the tissue, the present device and method propose to use an electro-osmotic effect applied within the blood vessels of the to-be-treated tissue or in adjacent tissue that shares blood vessels with the to-be-treated tissue. The present disclosure, in some embodiments, is directed to the application of current sufficient that electrical charge sufficient for the desired electro-osmotic effect is delivered only to the epidermis and dermis 120. In other embodiments, current may be sufficient so as to deliver electrical charge to the epidermis and dermis 20 and the subcutaneous layer 121. Whatever layers of skin receive electrical charge, the electrical charge and resulting fields may interact with the blood capillaries and vessels located therein to use an electro-osmotic effect to cause vibration in blood vessels.

Electro-Osmotic Flow in Capillaries and Vessels

As is known and appreciated in the art, and as described above with respect to FIG. 1, blood flows through the vessels 121b and capillaries 121a of the skin in order to deliver oxygen and nutrients and remove wastes. Blood flow is typically driven by the pumping action of the heart, wherein a pressure gradient within the vessels and capillaries causes blood to move and flow therewithin. However, a pressure gradient caused by a pumping action at some point in a circulatory system is not the only way to cause fluid flow within small channels, such as vessels and capillaries. Fluid flow may also be induced by electro-osmosis.

Figure 2:
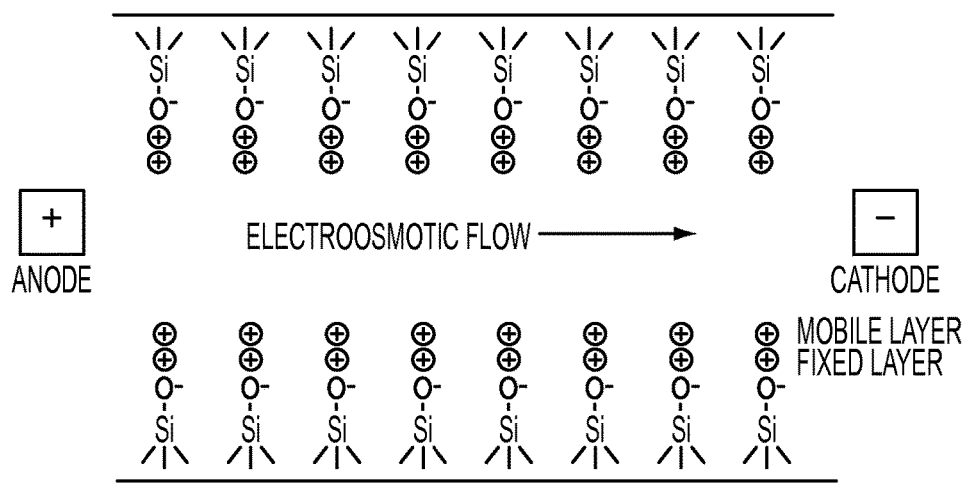
FIG. 2 is a schematic illustration of an example of electro-osmotic flow, in particular the flow in a fused-silica gel capillary in the presence of a buffer solution.

Electro-osmotic flow is the motion of liquid induced by an applied electrical potential across a porous material, capillary tube, membrane, micro-channel, or any other fluid conduit. Electro-osmotic flow is caused by the Coulomb force induced by an electric field on net mobile electric charge in a solution. Because the chemical equilibrium between a solid surface and an electrolyte solution typically leads to the interface acquiring a net fixed electrical charge, a layer of mobile ions, known as an electrical double layer or Debye layer, forms in the region near the interface. When an electric field is applied to the fluid, the net charge in the electrical double layer is induced to move by the resulting Coulomb force. FIG. 2 shows a schematic illustration of an example of electro-osmotic flow, in particular the flow in a fused-silica gel capillary in the presence of a buffer solution.

Because electro-osmotic velocities are independent of conduit size, as long as the double layer is much smaller than the characteristic length scale of the channel, electro-osmotic flow is most significant when in small channels.

The resulting flow from applying a voltage in a small channel is a plug flow. Unlike a parabolic profile flow generated from a pressure differential, a plug flow's velocity profile is approximately planar, with slight variation near the electric double layer. (See FIGS. 3a and 3b, discussed in greater detail below). This offers significantly less deleterious dispersive effects. Electro-osmotic flow through micro channels, for example, vessels and capillaries, can be modeled after the Navier-Stokes equation with the driving force deriving from the electric field and not the pressure differential.

Because electro-osmotic flow is an induced flow, it exists only so long as, and to the extent, the electrical field is applied to the subject micro-channel. For example, where no pressure gradient is applied, fluid will only flow in the channel when there is an electrical field present. Furthermore, fluid will flow to a relatively greater extent where a relatively greater field is applied, and to a relatively lesser extent where a relatively lesser field is applied. Thus, different patterns of fluid flow can be induced in by inducing more or less electro-osmotic flow. Examples of various flow patterns that can be induced in this manner may include, but are not limited to, stepped flows, intermittent flows, and cyclic flows. With electrical fields and currents of sufficient strength, flow patterns can be induced in layers of tissue targeted for treatment by improved electro-osmotic blood flow.

Physical Vibration Causing Increased Blood Flow

It is known in the art that blood flow can be increased by a variety of methods. For example, a class of drugs known as vasodilators can be used to treat a human patient, resulting in dilated blood vessels that yield increasing blood flow. More recently, investigations have been made into physical methods for increasing blood flow.

For example, it was reported by Kerschan-Schindl et al. (Clinical Physiology 21: 377-382 (2001)) that physical vibration can lead to increased blood flow volume. In this study, the subjects were exposed to whole-body vibration. They stood on a platform on a sagittal axle which alternately pushes the right and left leg upwards and downwards at a frequency of 26 Hz. Three sets of different positions were used.

This study discovered that a few minutes-lasting stance on a vibrating platform leads to an increase in the relative moving blood volume measured. Mean blood flow in the in the popliteal artery was also increased and its resistive index decreased. Furthermore, neither heart rate nor blood pressure was increased as a result of the exposure to vibration. Rather, solely peripheral circulation was affected.

In another example, Maloney-Hinds et al. (Medical Science Monitor 14(3), CR 112-116 (2008)) took the research of Kerschan-Schindl et al. one step further and investigated the effect of various frequencies and durations of physical vibration on the increase in blood flow observed. In particular, this study was conducted using vibration at 30 Hz and at 50 Hz, over time periods ranging from 1 to 10 minutes. It was discovered that both frequencies produced significant increases in skin blood flow within the first four minutes of vibration. Peak skin blood flow was achieved in the fifth minute. During vibration, the 30 Hz and the 50 Hz vibrations produced similar results, but the 50 Hz vibrations resulted in above-baseline blood flow for a longer period of time after vibration stopped.

It is presently known that increased blood flow from mechanical vibration is a result of increased production of endothelial nitric oxide synthase (eNOS) in the skin in the area of the blood vessels. See Kerschan-Schindl et al. cited above. eNOS has the effect of bioactively stimulating blood flow, and is produced as a direct result of applied mechanical vibration to the skin. Thus, it is observed, as in the studies above, that following a period of applied mechanical vibration, increased blood flow results in areas local to the vibration.

However, physical vibration methods such as those used in the above-referenced studies, and others, are applied externally and are largely impractical for home use by persons who want to increase blood flow. The devices employed in the studies used large electrical motors to cause the vibration, and resulted in the participants standing in an awkward position on a vibration device for extended periods of time. Use of a handheld vibrator (such as for massage), while also possible, applies vibration that may be hard to control, as the frequency of most vibrators will be affected by variation in the pressure of application to tissue and nature of the tissue to which the vibration is applied (e.g., fatty vs. muscular tissue, tissue depth). The vibrator applies vibration at the skin surface touched by the vibrator, with possible abrasion, and may also be accompanied by undesired noise. Thus, these methods would not be desirable for the average person to conduct in their own home on a regular basis.

Blood Flow Stimulating Device

It was discovered that mechanical devices are not needed to cause a physical vibration to increase blood flow within areas of the dermis and hypodermis targeted for cellulite or similar conditions. Rather, it was discovered that it is possible to create a sustained vibration-like effect within the skin through the controlled inducement of electro-osmotic flow within the capillaries and vessels within the skin. By rapid, cyclic osmotic blood flow within the blood vessels of skin to be treated, at a desired frequency, a movement of the blood within the vessels and capillaries is induced that is akin to applying external vibration. The voltage applied to create the electro-osmotic flow is sufficient to produce in blood vessels of the skin electro-osmotic pressure/velocity wavefronts corresponding to the cycling frequency, and these electro-osmotic wavefronts produce a mechanical action in the walls of blood vessels where they are produced. While the increased blood flow appears suited to address the vascular causes of cellulite, it will be seen that other conditions caused or aggravated by low blood flow and the resulting lowered levels of nutrition delivery and waste removal, also may be alleviated by the present method.

The method disclosed can be practiced by using first and second electrodes placed so as to deliver current through the tissue to be treated and by applying to the electrodes a varying current, with a waveform and magnitude that causes a varying electro-osmotic flow within blood vessels in the tissue to be treated or in tissue that shares blood vessels with the tissue to be treated. Unlike electrophoresis or TENS, the application of the current is not intended to deliver ions into tissues or influence nerves, but to "vibrate" blood vessels in the target tissue. Thus, if the to-be-treated area is an outer thigh, a first electrode placed on the outer thigh and a second electrode placed on the opposite side of the thigh would target current flow to the to-be-treated area. This would suggest a device with a current generating unit with two output wires, one for each of the first and second electrodes for carrying out the method.

For user convenience, a unitary, hand-held device may be desirable. Handheld galvanic skin treatment devices have been used for iontoforesis. Thus, the general format is familiar to users. It was found that such an existing handheld galvanic skin treatment device can be modified by modifying the electronics to output a varying current, with a waveform and magnitude that causes a varying electro-osmotic flow within blood vessels in the tissue where improved blood flow is desired. The current levels available from such a handheld device, appear sufficient to induce the desired pressure wavefronts within the vessels and capillaries of the skin region to be treated, and thus the desired mechanical action akin to external vibration, to enhance blood flow and induce eNOS generation. Various embodiments of such a skin treatment device will now be discussed.

Figure 4:
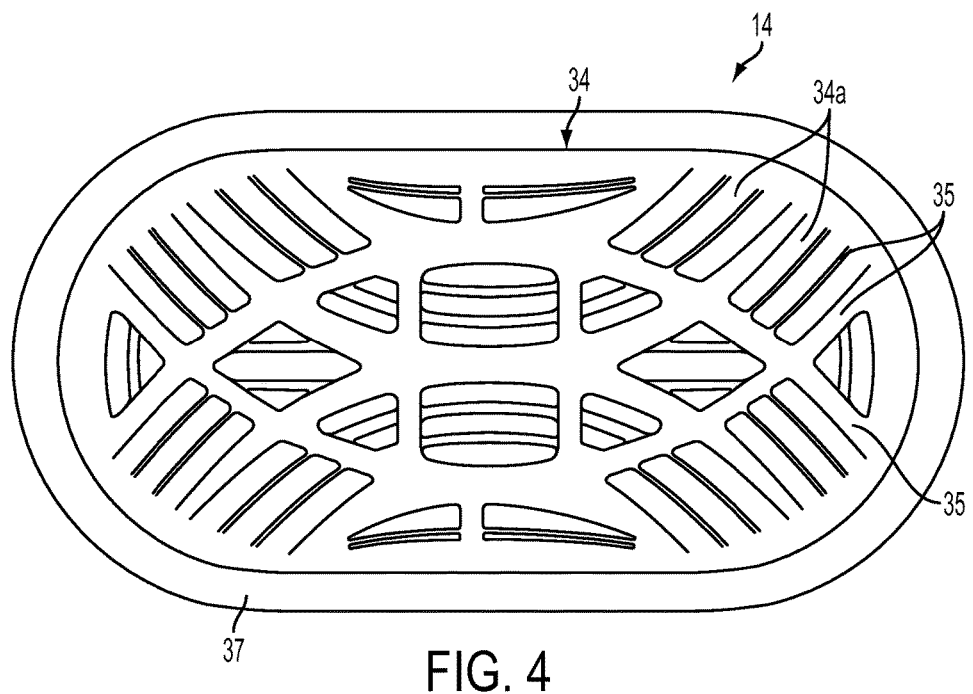
FIG. 4. shows a plan view of the skin electrode face of an illustrative skin treatment device.

One embodiment of a unitary handheld electronic skin treatment device for electro-osmotic effect is disclosed in FIGS. 4 through 7. Referring particularly to FIG. 4, this shows the skin electrode side or face of a handheld skin treatment device 14. The skin electrode 34 (or first electrode) occupies most of this side. The skin electrode 34 is made of a conductive material suitable for skin contact. As can be seen, the surface of the electrode 34 may have a pattern of bumps, ridges or raised portions 34a, separated by channels 35. These may help in establishing good electrical contact with skin that is not flat and/or not smooth, particularly when used with an electroconductive gel. The pattern may also help in distributing and stirring the electroconductive gel during gentle circular movement of the electrode 34 on the skin. The periphery of the skin electrode face is formed by the edge of the plastic housing 37 of the device. This housing 37 is non-conductive, thus isolating the electrode 34 from other parts of the device 14.

Figure 5:
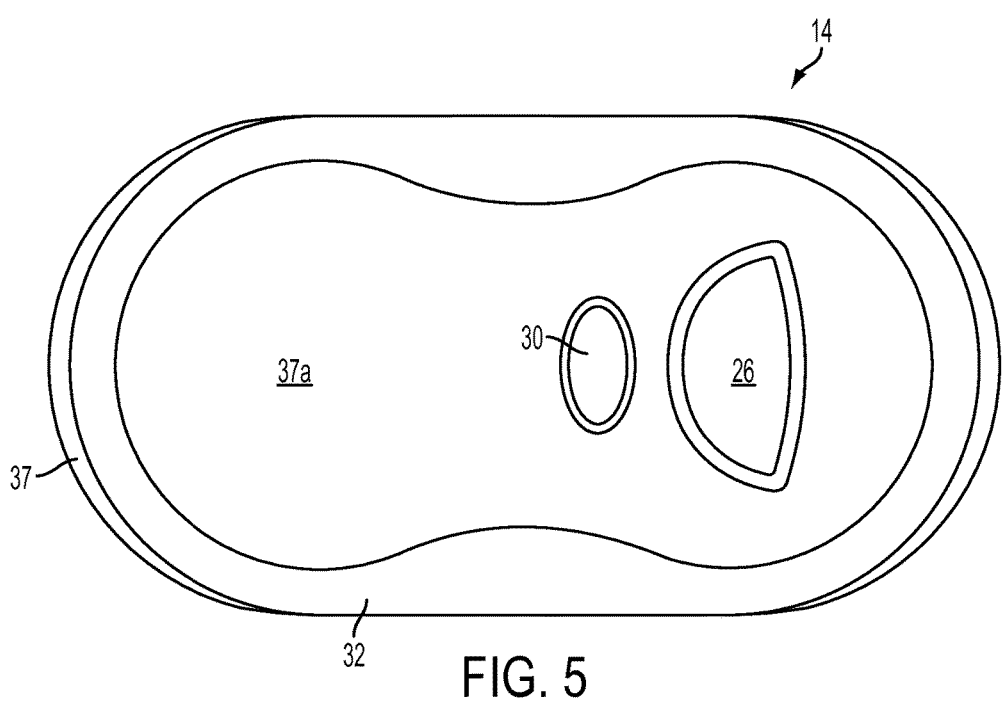
FIG. 5 shows a plan view of the display and control face of an illustrative skin treatment device.

FIG. 5 shows the display and control side or face of the skin treatment device 14, which is opposite the skin electrode 34. Most of this side is made up of a panel 37a of the plastic housing 37. Within this panel 37a is a display 26, which may be an LCD screen or similar electronic display, and a control button 30. The control button is used to turn the device on and off. If the internal control circuitry is configured to sense button hold duration or count button presses, the control button may also be used for selection of options that the user can cycle through on the display 26. (In an alternative, not shown in FIG. 5, there can be a second control button for selection of displayed options.) For example, after being turned on, the device may display one or more power levels, or one or more session duration timers. Icons on the display may show on/off status and the selection of a power level, timer value or other options. The periphery of the display and control side of the device 14 is formed by a hand electrode 32 (or second electrode). The hand electrode 32, like the skin electrode 34, is made of a conductive material suitable for skin contact. As can be seen, the surface of the hand electrode 32 is wider near the middle of the two longer sides. At these wider points, the hand electrode 32 extends down onto the right and left sides of the device, to give the hand electrode greater surface area than just the surface area it occupies on the display and control side of the device.

Figure 6:
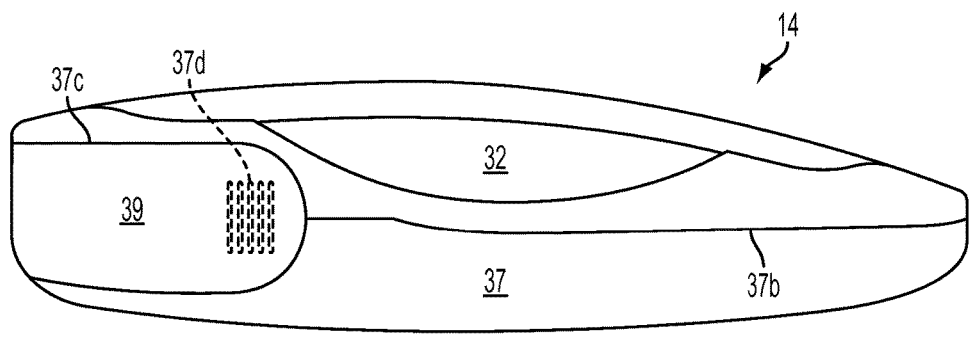
FIG. 6 is a left side view of the skin treatment device.
Figure 7:
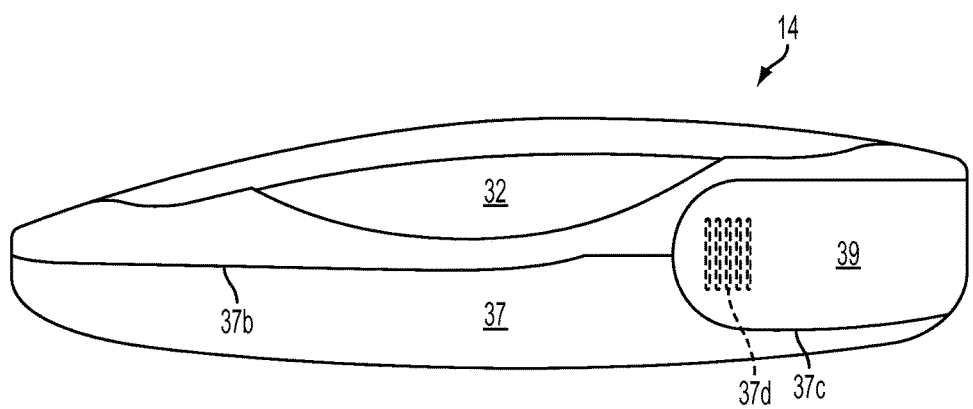
FIG. 7 is an right side view of the skin treatment device.

FIGS. 6 and 7 show the left and right sides, respectively, of the skin treatment device 14. Here one can see the generally crescent-shaped extensions of the hand electrode 32 extending about one-third or one half the way down onto the right and left sides of the device 14. Other features visible on the sides are a parting line 37b at which upper and lower halves of the housing 37 are joined. Also visible are the periphery 37c and gripping protrusions 37d of an access panel 39. When the access panel 39 is removed, the user may access a removable battery (which may be rechargeable) and any other controls that the designer may choose to place on the interior of the device, such those used for calibration or a maximum power setting that may be set differently for different types of operation or user characteristics, such as weight or tissue conductivity.

Thus, in FIGS. 4 to 7, the first and second (hand and skin) electrodes 34, 32 employed in the skin treatment process are shown. The hand engaging electrode 32 is located primarily on the display and control surface of the skin treatment device 14, and the skin treatment electrode 34 is located on the opposite face of the treatment device 14. In the course of actual electrical skin treatment, the electrical circuit extends between a current driver output of the control circuit of the treatment device 14 through the skin treatment electrode 34 (which is moved over the to-be-treated skin area), through the body of the user and back through the hand or palm-engaging electrode 32, to the current driver circuit of the treatment device 14.

Figure 9:
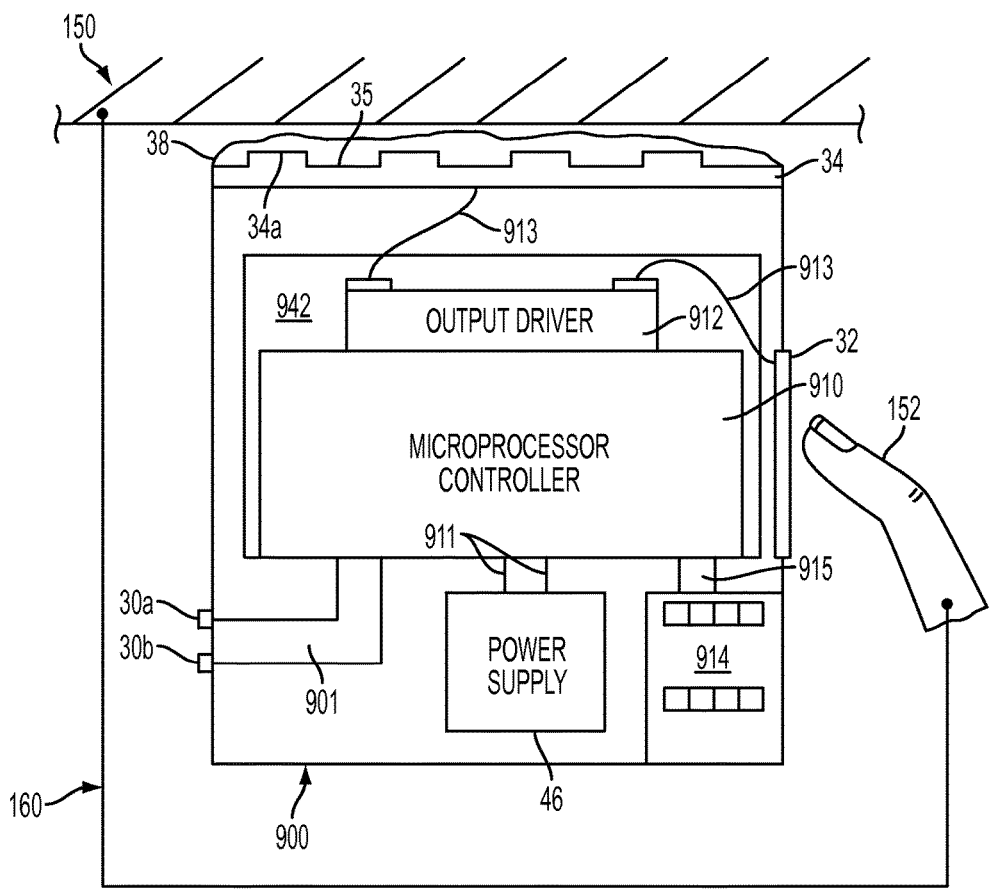
FIG. 9 is a schematic block diagram of the electronic components of the skin treatment device.

FIG. 9 shows a schematic block diagram illustrating the components and operation of an example electronic skin treatment device 900 for self application. There is a printed circuit board (PCB) 942 mounted within the treatment device 900. The PCB 942 has a microprocessor controller 910 mounted thereon, for executing a software program to control an output driver and other electronic circuitry and to provide various functions or modes of operation. The microprocessor 910, the software program, the electronic circuitry, and the various modes of operations will be described in more detail below.

As shown, a power supply, such as a battery 46 connects via wires 911 to a microprocessor controller 910 with an output driver 912. The driver 912 provides the treatment current from its output connections 913 to a first electrode, the skin electrode 34, and a second electrode, the hand electrode 32, used to complete a circuit through the body of the person treated. The skin electrode 34 is placed at the surface of the skin region 150 to be treated. One or more fingers 152 of the user may be in contact with the second electrode, such that a current path 160 becomes available through the body of the person being treated. Control buttons such as an on-off switch 30a and an option selection button 30b, e.g., for selecting current level, may be connected to the microprocessor controller 910 by a bus 901. The display 914 may be connected to microprocessor controller 910 by a bus 915, for display of on-off status, power level, a treatment timer or other user information. The microprocessor controller 910 may include a suitable processor, memory for storing control software (software program modules) that determines the shape and strength of the output signal from output driver 912 and controls other functions and has connections to busses for receiving inputs and delivering outputs, such as input from a current level sensor (not shown). The microprocessor controller 910 is configured by the stored control program and its execution to provide the various features of the disclosed skin treatment device, including the delivery from output driver 912 of an electrical current between the head 34 and the second electrode 32 at a level and with a waveform pattern as will be discussed in greater detail below.

Various geometric patterns may be employed on the skin treatment electrode 34 both for aesthetic effect and to increase effectiveness and/or the comfort of the user. Of course, other head designs are possible, including those that lack any patterned features.

Where a pattern of raised bumps 34a with separating channels 35 is used on head 34, the pattern may be chosen so as to promote even distribution of and effective stirring of a conductive gel 38 that may be used with the device. Such gels may be electroconductive and used to help improve electrical contact between the head 34 and the skin 150 to be treated. Such gels also may optionally include active materials to be driven into the skin for various purposes discussed in greater detail below. In either case, the pattern on the head 34 may be chosen so that a generally circular rubbing motion on the skin 150 will provide even distribution and a stirring motion for the gel 38, so that all areas of the head 34 are well-coated with a layer of the gel and the gel in any given area is refreshed on a continuing basis by gel from adjacent areas. An example of an electroconductive gel is SpectraGel 360-Electrode Gel™ by Parker Labs. Other examples are Galvanic Pre-Treatment Gel™ and ageLOC Bodying Shaping Gel™, from Nu Skin Enterprises, Inc. Other aqueous-based gels containing ionic molecules will also work to aid forming a conductive path between the head 34 and the tissue region to be treated.

Figure 8:
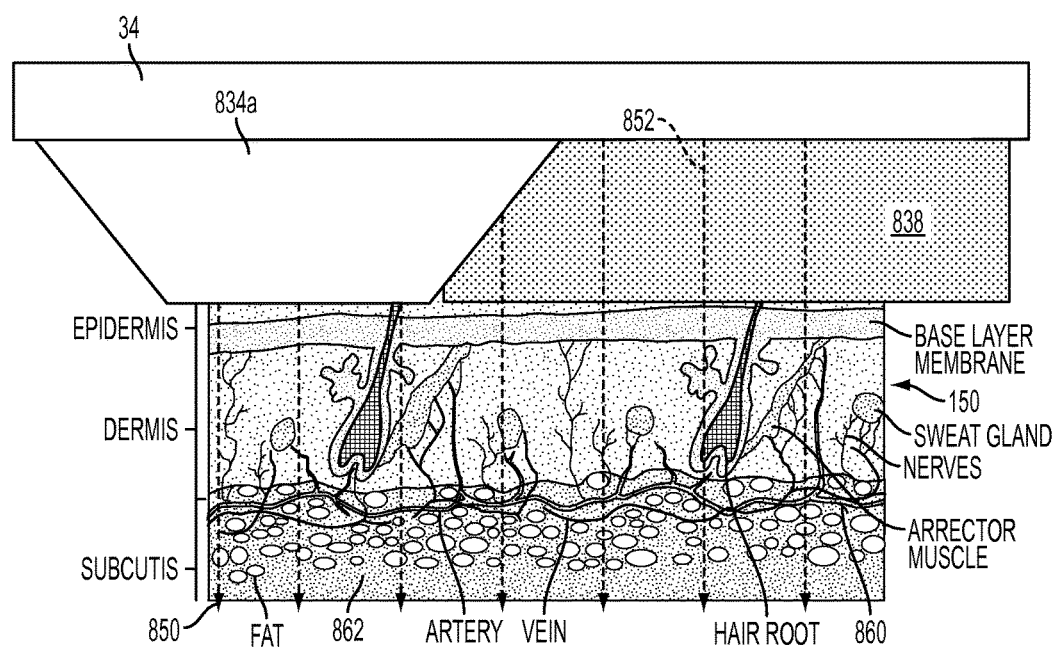
FIG. 8 is an close-up view of skin being contacted with the skin treatment device, showing the current flow that leads to the fields resulting in electro-osmotic flow.

FIG. 8 shows a schematic detail view of a skin cross-section 150 in contact with a ridge 834a of the skin electrode 34 and with a pocket of conductive gel 838 in the channel adjacent the ridge 834a. The projection of the current and the corresponding electric fields into the skin 150 to influence the blood flow in blood vessels 860 will be explained in greater detail below.

Electrical Current Effected by Handheld Device

Referring again to FIG. 9, in one embodiment of the present disclosure, to deliver current to the tissue region to be treated the apparatus 900 may employ a first electrode or skin electrode 34 and at least one other electrode, in one embodiment a second or hand electrode 32 on the body of the apparatus 900, where the user's hand may grip the apparatus during use. In use, current flows between the first electrode 34, through the contact surface between the user's skin and electrode 34 at the point of application of the electrode 34 to the skin and further into the skin and through the user's body to the hand of the user that is grasping the second electrode 32 of the apparatus. With good contact between the surface where the skin electrode 34 of the device is applied and the second electrode 32 portion of the device contacted by the gripping hand of the user, the user's body completes the current path 160 between electrodes. Depending on the current provided, a current density may be specified as flowing across the skin surface contacted by the skin electrode 34. It flows through the epidermis and dermis and into the adipose tissue or hypodermis below these.

Blood is a biologic tissue that is composed largely of water and ions and is consequently the best electrical conductor of all the tissues. Muscle is composed of about 75% water and depends on the movement of ions for contraction. Muscle tends to propagate an electrical impulse much more effectively in a longitudinal direction than transversely. Muscle tendons are considerably more dense than muscle, contain relatively little water, and are considered poor conductors. Fat contains only about 14% water and is thought to be a poor conductor. Peripheral nerve conductivity is approximately 6 times that of muscle. However, the nerve is generally surrounded by fat and a fibrous sheath, both of which are considered to be poor conductors. Bone is extremely dense, contains only about 5% water, and is considered to be the poorest biologic conductor of electrical current. Thus, it would appear that a body that has current introduced in a treatment region will provide a current path varying by tissues type but adequate in blood vessels and other tissue types to carry at least a limited flow of current to another point of contact on the body that completes a current path. Further, the vessels that carry blood and are part of the current path apparently will be preferential carriers of the electrical current and thus, have stronger electrical fields corresponding to the current than other tissues. More particularly, in tissue containing fat cells and blood vessels that are part of a current path, it would appear that the blood vessels will be preferred paths for the current.

FIG. 8 shows schematically how a skin electrode 34, with a ridge 834a contacts the skin 150 and a pocket of electroconductive gel 838 adjacent ridge 834a can assist in making broader electrical contact with the skin. FIG. 8 shows a plurality of lines 850 representing current flow from the ridge 834a and lines 852 representing current flow across the gel-filled channel adjacent ridge 834a of skin electrode 834 with both current paths penetrating into the skin. Although FIG. 8 shows by the direction of the arrows current entering the skin 150, depending on polarity, the current may flow the other direction. But with either direction of flow, corresponding electrical fields will be induced in the skin tissue, and these will at some level of strength be present at and in at least a portion of the blood vessels 860. This may to some extent depend on the orientation of a blood vessel relative to the flow direction of the current. FIG. 8 is idealized in showing current flow as uniform and equal across various tissue types. In fact, current direction and strength will vary as the current follows the path of least resistance through the tissue and also diffuses away from the electrode contact area where the current is introduced and enters the user's body. However, the penetration of the current into the skin will occur as it follows a circuit through the user's body.

Figure 11:
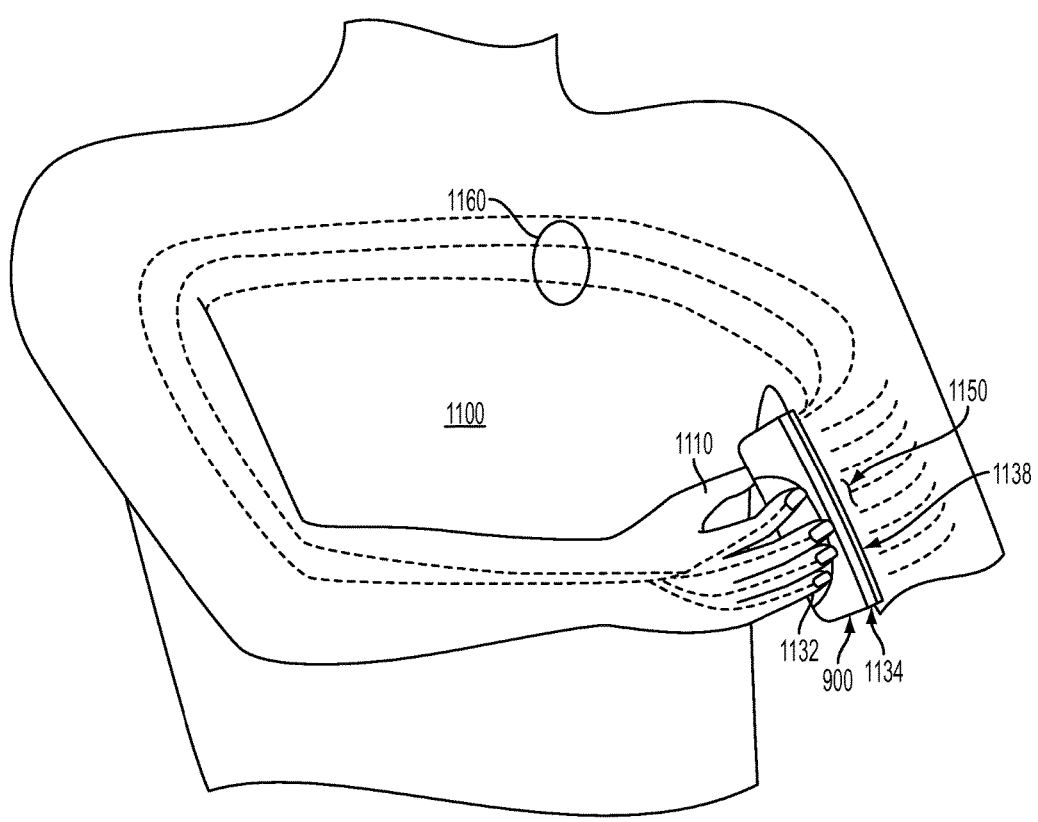
FIG. 11 is an schematic illustration of a skin treatment device delivering current to a treatment region of a user with current flow through the user's body.

In one example, illustrated in FIG. 11, a right-handed user may grip the apparatus 900 in her right hand 1110, which contacts a hand electrode 1132 on one side of the apparatus. The user may apply the apparatus to a skin treatment region 1150 on the user's left upper arm. In this example, current may flow from the skin electrode 1134 of the apparatus 900 into the left upper arm of the user. Part of the current path may be through a conductive gel 1138, where direct contact of the metal of the skin electrode 1134 to tissue is not occurring. From the skin contact interface at skin electrode 1134, the current may travel and spread through the user's shoulder and torso and then into the user's right arm. In the right arm, it may travel into the apparatus-gripping right hand, and converge for flow back into the apparatus 900 at the second electrode. In this manner, an electrical circuit through the body, as generally indicated at 1160, is completed between the first and second electrodes of the apparatus 900, allowing current in the waveform described below to flow in the desired skin treatment region, to cause the electro-osmotic effects on blood flow described above.

In a preferred embodiment of the device, the treating surface or skin electrode head 1134 has surface area dimension of approximately 2.5 inches by 5 inches; however, other smaller or larger surface areas may be used. The active portion of the treating surface or skin electrode 1134 may be made of a conductive metal, such as copper, silver, gold, aluminum, iron, zinc, nickel or magnesium, or other conductive metals and alloys made from these, such as zinc-copper or silver copper or made of an electroconductive plastic. In a one embodiment the treating surface or skin electrode 1134 is made of plastic plated with a conductive chrome alloy, such as a chrome-nickel or copper-chrome alloy. The head/hand electrode 1132 may be made from the same material. Such head/hand electrode 1132 may be placed on a portion of the apparatus 900 electrically separated by insulating material (such as a portion of a non-conductive plastic case) from the location of the skin treating surface or skin electrode 1134, such as on the top and side portions of the device.

In an alternative embodiment, multiple small electrode pairs on or in the skin treating surface 1134 provide a means for the handheld device to deliver an electric current into the skin generally between the electrodes in a pair in a controlled manner. One or more pairs may be employed in any embodiment. In alternative embodiments, electrical components other than electrode pairs may be employed to introduce the desired current flow into tissue. These include, for example, electroconductive patches or other means of contacting skin by which a current or field may be introduced into the skin sufficient to cause an electro-osmotic flow within the blood vessels of the to-be-treated tissue or in adjacent tissue that shares blood vessels with the to-be-treated tissue.

Figure 10A:
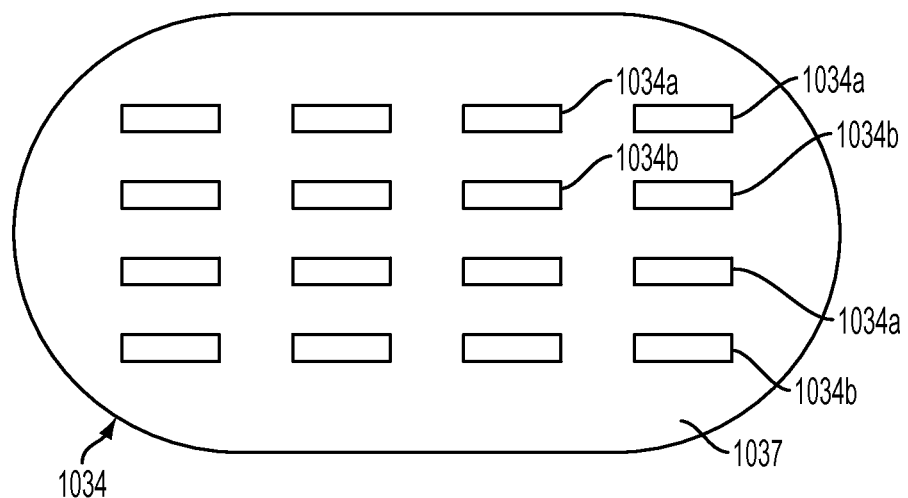
FIGS. 10a and 10b are schematic diagrams showing an example skin treatment face with cathode-anode electrode pairs on a common surface and how such a pair supplies current into a skin area to be treated.
Figure 10B:
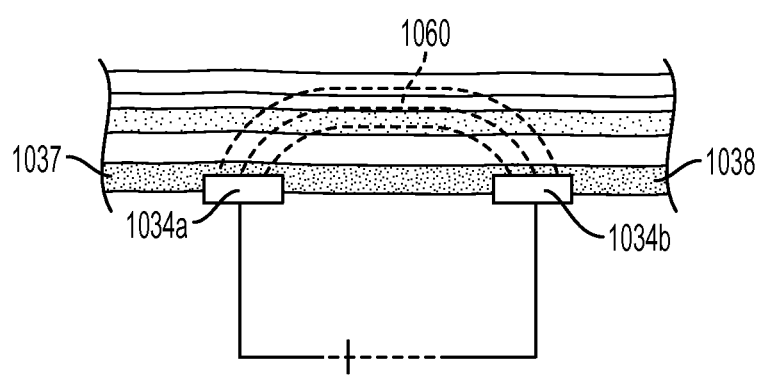

In one embodiment shown in FIGS. 10a-10b, the presently disclosed skin treatment device includes a skin treating surface 1034 with a substrate 1037 that is generally non-conductive but includes a plurality of discrete electrode pairs 1034a-1034b, each electrode pair including a first conductive electrode 1034a that is an anode in electronic communication with a second conductive electrode that is a cathode 1034b. (Anode and cathode reverse roles with alternating current patterns.)

The conductive electrodes of such pairs may be formed at the treating surface or head 1034 using any one of a variety of techniques known in the art. For example, one or both of the first and second conductive electrodes may be a piece of metal sheet, wire or mesh, or a metal-coated fabric or other material such as a fabric coated with a metal. Alternatively, the first and second conductive electrodes may be deposited on a substrate 1037 by chemical or electrochemical deposition, such as electrolytic plating for chemical deposition and electroplating for electrochemical deposition as known in the art. The first and second conductive electrodes may be deposited on a substrate by physical deposition, such as screen printing, spray coating, gravure printing, laser jet printing, pad printing, needle printing, dip coating, vacuum deposition, or other printing or transfer processes. In each case, the electrodes may be connected to the driver circuit that supplies current as described above.

As can be seen in FIG. 10b, showing a cross-sectional view of contact between a treating substrate 1037 with an electrode pair 1034a-1034b, when there is a difference in electrical potential applied across the electrode pair 1034a-1034b, a current 1060 flows through the skin that lies between the two electrodes. A gel 1038 may assist in making a lower resistance current path between electrode pair 1034a-1034b. An array of such electrode pairs as seen in FIG. 10a allows a larger skin treatment area to receive current.

Electric current output of the apparatus may vary depending on the treatment duration and the size of the electrodes in contact with the skin. In general, for longer treatment durations, a lower current output may be used. In addition, the larger the size of the electrodes the higher the current output that may be comfortably supplied, because the current density per unit area of electrodes is reduced by the larger area. In one embodiment, the apparatus may have a current sensing component, e.g., as part of the output driver in FIG. 9 and providing an input to the microcontroller. The current sensing component may be configured to detect the flow of current in the apparatus in either the apparatus/body circuit embodiment or the electrode couple embodiment. The sensing component may provide a signal that is measured at the microcontroller and if measured as too low, software logic in the microcontroller may adjust the apparatus so as to increase the current flow until a desired current flow is detected; alternatively, the microcontroller may decrease the current flow where a higher than desired current flow is detected. In this manner, the device is able to automatically maintain a desired current flow in the body without control input from a user, no matter where the apparatus is applied on the body.

Application of Electrical Current

As described above, current may be applied to the skin by the various embodiments of the skin treatment device, traveling from the outer layers of electrode contact into the skin layers of the treatment region where fat cells are present, or into the adjacent layers that share blood vessels with the layer containing fat cells. Thus, the current introduced at skin electrode 34 (FIG. 9) or 1134 (FIG. 11) or at substrate 1037 (FIG. 10) flows through the epidermis and dermis and into the subcutaneous layer. The current is selected to induce an interrupted or discontinuous electro-osmotic flow in the vessels and capillaries of the skin in a controlled manner, resulting in vibration-like forces in a manner so as to increase blood flow within the skin. In particular, the user activates the device 900 so as to apply between the electrodes (e.g., 1134, 1132 in FIG. 11) a current that has a pulse component from a signal generating circuit. This circuit may have an output in generally the form of a square wave as observed at the outputs of driver 912. Each cycle of the square wave may last between 1 and 100 milliseconds, resulting in a fundamental frequency of 10 to 1000 Hz; other frequencies may be used, whereby the current applied in the skin is sufficient to produce voltages and electro-osmotic pressure/velocity wavefronts corresponding to the fundamental frequency in blood vessels of the skin to be treated. In one embodiment the current is AC with pulses of positive and negative polarity, no DC component. In another embodiment the AC current has a DC component, or the pulses may be a varying DC current.

A velocity wavefront, as used herein, indicates any increase in the volumetric flow rate of blood within a vessel or capillary as observed passing through an arbitrary cross-sectional plane of such vessel or capillary. This increase in volumetric flow rate results in a local increase in momentum within such vessel or capillary, as it will be appreciated that momentum may be defined as the mass of blood flowing multiplied by its velocity. Further, any change in momentum, such as would be induced by electro-osmosis as described above, results in a corresponding force exerted within the capillary or vessel. As capillaries and vessels are not rigid conduits, the application of such force results in the vessels expanding and contracting, corresponding with the application and subsequent removal of such induced force. Again, this will correspond with the frequency of the application of an applied current across the vessel or capillary. The ultimate result, therefore, is an induced mechanical effect akin to vibration originating within the vessels or capillaries, due to the forces applied by the blood therein against the conduit walls.

Various patterns of applied current may be used. As noted, either alternating current or direct current may be used, or alternating current with a direct current component may be used. The first electrode may be positive and the second negative, or vice versa. The skin treatment device may provide current anywhere between −0.500 mA and 0.500 mA, but in one embodiment the current may be about a root mean square (RMS) current application ranging between about 0.100 to 0.500 mA or, may be an RMS current application of between about 0.125 mA and 0.400 mA. In some applications an RMS current ranging between 0.100 to 5.0 mA (RMS) may be used, if patient comfort is maintained. The applied current will cycle between two values so as to create cyclic variations in blood flow within the capillaries. Cycling between two values can occur at 10 Hz, 20 Hz, 30 Hz, 40 Hz, 50 Hz, 60 Hz, 70 Hz, 80 Hz, 90 Hz, 100 Hz, or other values between 1 and 100 Hz. These are fundamental frequencies, as the signal is not normally a pure sine wave and thus contains other frequency components. Thus, as used herein, an output current with a waveform having a fundamental frequency means a waveform that has a pulse or other main component that repeats at the fundamental frequency, but the waveform may contain many other frequencies. Current can remain at the waveform peak level for periods of time ranging from 1 mS to 100 mS, or between 3 mS to 30 mS or 5 mS to 50 mS.

Figure 12:
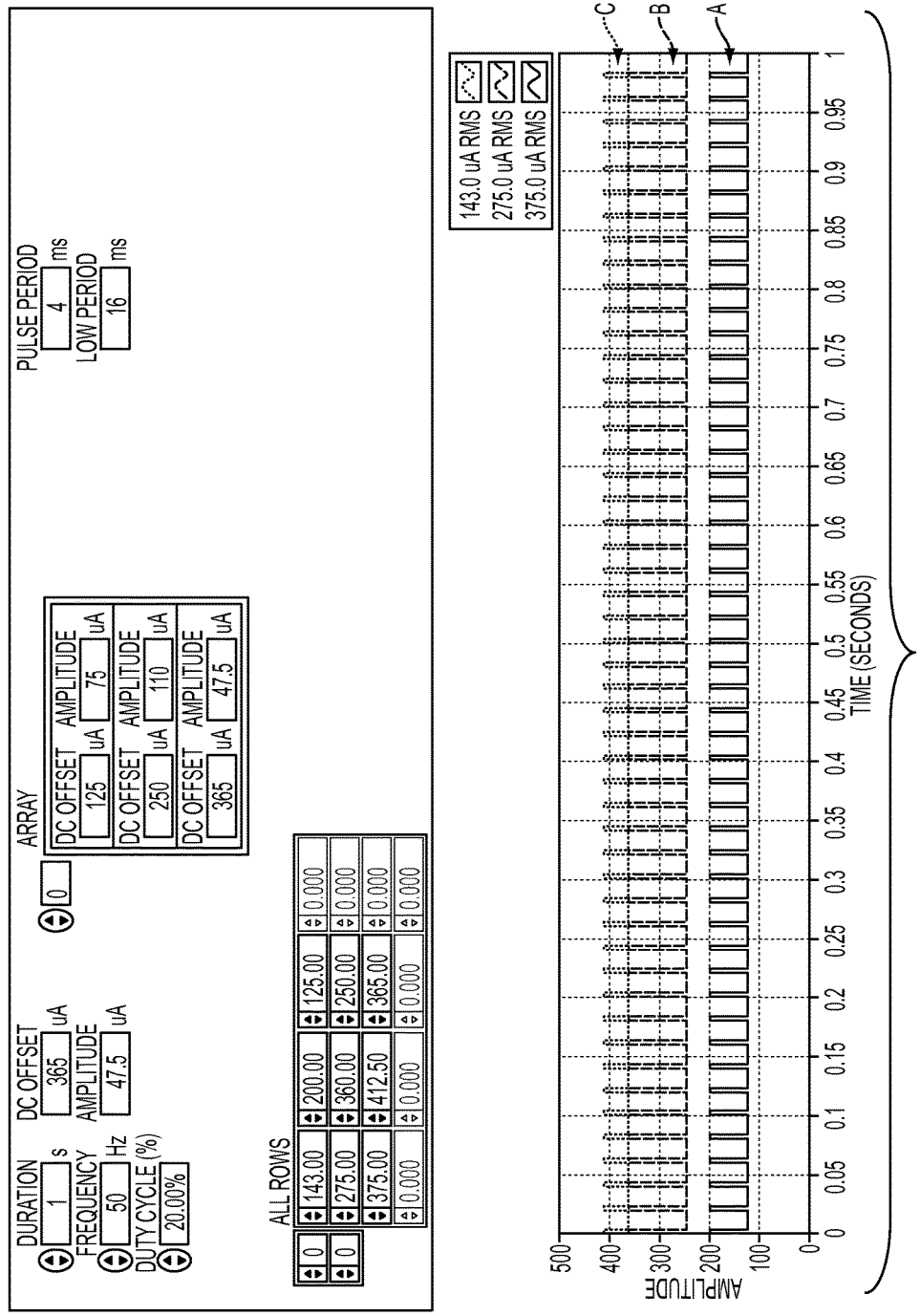
FIG. 12 is a diagram showing particular current signals suitable for use with the present disclosure.

FIG. 12 illustrates the waveform pattern of one embodiment. The waveform in FIG. 12 may be described as consisting of DC square wave pulses, but other waveforms may be used, such as sawtooth, triangular, or trapezoidal, or combinations of these waveforms. In one particular embodiment shown in FIG. 12, waveform "A", the current cycles between 0.200 mA and 0.125 mA, remaining at the former for about 4 mS, and the latter for about 16 mS, resulting in a root mean square current application of 0.143 mA. In another embodiment, waveform "B", the current cycles between 0.360 mA and 0.250 mA, remaining at the former for about 4 mS, and the latter for about 16 mS, resulting in a root mean square current application of 0.275 mA. In yet another embodiment, waveform "C", the current cycles between 0.412 mA and 0.365 mA, remaining at the former for 4 mS, and the latter for 16 mS, resulting in a root mean square current application of 0.375 mA. In one embodiment, selection among the available current patterns or levels can be made by manipulating the control button 30 on the device 14 (see FIG. 5). Alternatively, the device may contain logic in microcontroller 910 that may be programmed to select a particular current level, after sensing the current level that flows with a given initial voltage or power output and a given user body "circuit".

If the blood flow increase effected by the above current levels is deemed less effective than desired in the target tissue, the current levels may be increased. The above levels are considered comfortable and have low levels of skin irritation or side effects with most users. However, user comfort is the main limit and may vary from user to user. Comfort may also be affected by the electro-conductive gel used. Levels in the range of 1 mA to 100 mA are used for various other forms of electrostimulation of humans. Thus, for selected patients or conditions in patients (e.g., the need to target tissue and blood vessels deeper into the body, where a current of the level stated above becomes too attenuated to produce the desired wavefronts) and assuming the discomfort level is not too high, a device as described herein might use pulsed current in the range 1 mA to 200 mA RMS or 1 mA to 500 mA RMS range, or any other ranges that have been found acceptable for various forms of electrostimulation of humans.

Figure 3A:
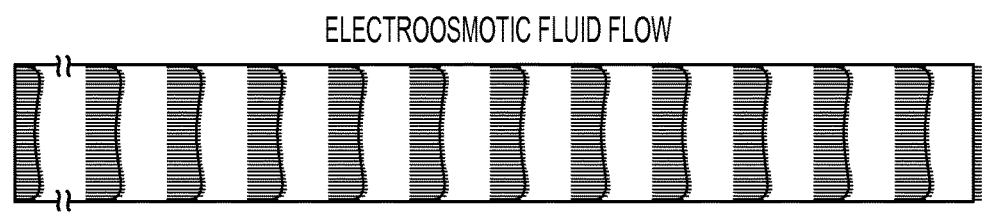
FIGS. 3a and 3b illustrate particular patterns of electro-osmotic fluid flow that results from application of the disclosed skin treatment device.
Figure 3B:
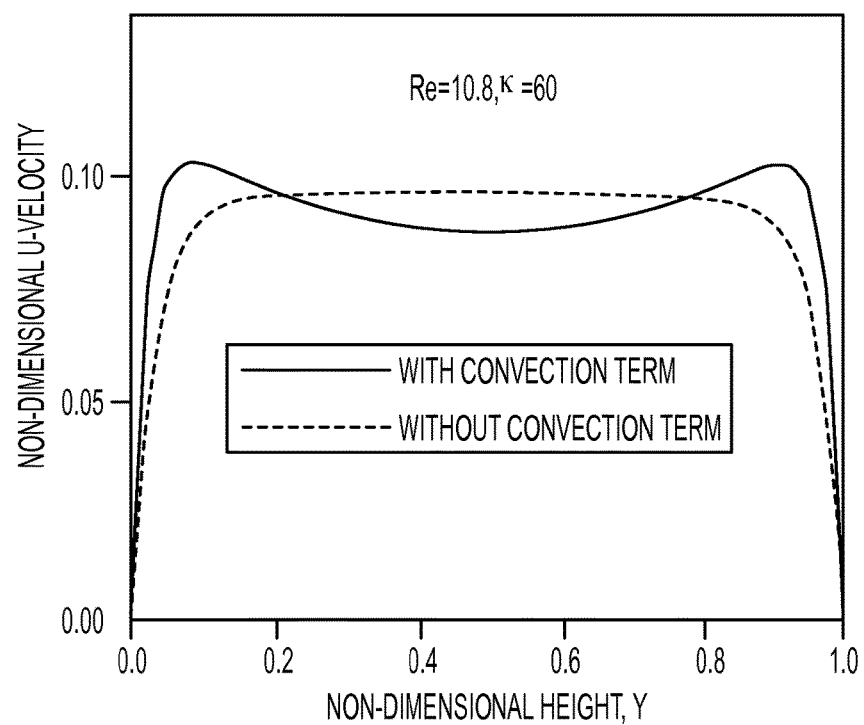

The current flowing in the tissue and/or blood will result in voltage differentials and charge accumulations within at least some portions of some blood vessels that cause electroosmotic flow. Because the current varies in level, the voltage differentials and the flow they cause will vary with the current level variations. The resulting varying flow within the blood vessels and capillaries is a plug flow with wavefronts at various intervals resultant from the applied current, as shown in FIG. 3a. Results of a theoretical calculation of a flow pattern, with and without convective terms accounted for, are depicted in FIG. 3b. These electro-osmotic wavefronts, when present in the capillaries and vessels of human skin, produce a mechanical action, akin to vibration in the walls of blood vessels where they are produced. This mechanical action or intravascular vibration, as discussed above, results in increased blood flow.

It is believed the present method of inducing vibration avoids the negative aspects of an instrument that causes physical vibration of the entire skin, including vigorous massage. Because the smallest blood vessels are most vulnerable to compression/damage, using a mechanical device that actively vibrates the skin, including the massaging action that would be used in conjunction, is likely to damage those tiny blood vessels and stretch the extracellular matrix (ECM, composed mostly of collagen and elastin fibers) to an increased damaged state. As the ECM is further damaged, it allows more herniation of the fat cells through the ECM and up towards the dermis/epidermis. Because women have vertical septae, the problem of cellulite appears, in part, because the fat cells press through (herniate) into the dermis, and because the ECM meshwork of the dermis is weak. If the fat cells are held in place by a strong ECM there is less herniation and elevation of the epidermis above.

By causing intra-vascular vibration via a pulsating electro-osmotic flow, the present method and device reduce the possibility of damaging further the tiny blood vessels that have been shown to be important in maintaining proper skin health and appearance, i.e., in not enhancing the development of cellulite. Also, by avoiding the use of external mechanical vibration of the skin, the present method and device avoid excessive stimulation of the neural components in the skin. The tie between the nerves in the skin and the metabolism of the skin is important and quite complicated. By using intra-vascular fluid vibration, the present method and device target the specific structure, the blood vessel and the specific cells, the endothelial cells lining the blood vessel. The present method and device are not vibrating the whole skin, and thus not vibrating the nerves, or lessening any nerve vibration.

Finally, the present method and device causes persisting beneficial effects with its eNOS generation. In a clinical study on nasal humming elevating eNOS, several periods of humming over several days was sufficient to improve rhinosinusitis. Strong humming for one hour daily was found to terminate chronic rhinosinusitis in four days: "A case report and hypothesis for action by stimulation of endogenous nasal nitric oxide production." Med Hypotheses, 2006; 66(4):851-4. Epub 2006 Jan. 10.

Example 1

A clinical study was conducted to evaluate the effectiveness of a device as shown in FIGS. 4-7 to improve blood flow in the skin in non-smoking women in general good health. A total of 10 Caucasian female subjects, between the ages of 20 and 35, completed the study. All subjects were required to have a BMI of 20-30 and a Fitzpatrick skin type of I-II. The device was used for five minutes, based on its built in timer and was set to deliver 0.1375 mA RMS, 0.275 mA RMS or 0.375 mA RMS current, with a square-wave DC pulse. Subjects participated in the following procedures at each indicated time point.

Laser Doppler Measurements. A Moor Laser Doppler MB3 was used to capture blood flux measurements on each leg. This process was repeated twice more so that each subject had 3 mean scores taken at the test site on each leg. Measurements were performed on the vascular area (pre-marked area, see below) at baseline prior to device application and at least 5 minutes post-application.

Chroma Meter Measurements. A Minolta Chroma Meter CR-400, in conjunction with a computer, was used to assess skin color. Measurements on the vascular area (pre-marked area, see below) of each leg were taken at baseline prior to device application and at least 5 minutes post-application.

Test Material Application. At baseline, clinic staff pre-marked a test size area of 100 square centimeters ($cm^2$) on each leg. Under clinic staff supervision, subjects applied the test gel to 1 area (1 test gel per leg-total of 2 test gels) and gently massaged into the skin on the right or left leg (according to pre-determined randomization) using the device.

The subjects applied Galvanic Pre-Treatment Gel™ and ageLOC Bodying Shaping Gel™, from Nu Skin Enterprises, Inc. in two different trials, one gel on each leg in each trial. The device was applied to the area with gel in a "figure-8" massage motion. Subjects participated in all of the following procedures on one leg followed by the other leg:

Test Site Designation. Clinic staff marked a test size area of 100 square centimeters on each leg. The test areas marked were vascular areas on dorsal surface of the upper legs and areas that had not been compressed by sitting or tight-fitting clothing.

Laser Doppler Measurements. A Moor Laser Doppler MB3 was used to capture blood flux measurements on the leg. Real time blood flow (flux) was monitored until a stable signal was obtained, and stable values were then recorded for approximately 60 seconds. The data collected during this time was averaged by the Moor MB3 software to produce a mean flux score. An increase in the values indicated an increase in blood flow. This process was repeated twice more so that each subject had 3 mean scores taken at test site on each leg. Measurements were performed on the vascular area (pre-marked area).

Chroma Meter Measurements. A Minolta Chroma Meter CR-400, in conjunction with a computer, was used to assess skin color. L* values described the relative brightness on a gray scale from black to white, and scores increased as the skin tone became brighter. a* values described the color hue ranging from red to green and scores increased with vascularization or blood flow. b* values described the color hue ranging from blue to yellow and scores increased with the amount of melanin in the skin. Triplicate measurements were performed on the vascular area (pre-marked area).

The results were as follows for Laser Doppler Measurements. Both test gels in conjunction with the Galvanic instrument produced significant improvements in blood flow (flux) values for all subjects at post-application when compared with baseline. No significant differences were found between treatments. The results were as follows for Chroma Meter Measurements. Statistical analysis of Chroma Meter a* values for both test gels in conjunction with the Galvanic instrument showed slight directional increases (not statistically significant) in blood flow at the post-application time point when compared with baseline values. (One reason for this may be that this instrument does not look as deeply into the tissues as the Laser Doppler instrument.) No significant differences were found between treatments. The tables in FIGS. 13 and 14 show the numerical results.

Optional Iontophoresis Added

In some embodiments, the current introduced for electro-osmotic flow also can be used for iontophoresis for delivery of an active substance in combination with intravascular vibration as discussed above. In accordance with one implementation, the method, system, or apparatus may include transdermal delivery or transport of a substance using an iontophoretic or galvanic current. The terms "iontophoresis" and "iontophoretic" as used herein refer to the introduction or transport of a substance such as a medicament into or through a skin, tissue, or other biological surface by the application of an electric current or electromotive force. According to one embodiment, the substance to be transported is completely charged, completely uncharged, or partly charged and partly uncharged. Alternatively, more than one substance can be transported, in which all of the substances are completely charged, completely uncharged, partially charged, or some of the substances are at least partially charged and some are uncharged.

According to one aspect, without being limited by theory, the transport of the substance is accomplished via electro-migration, electro-osmosis, or some combination of the two. It is understood that "electro-osmosis" has also been referred to as electrohydroconesis, electro-convection, and electrically-induced osmosis. In one embodiment, electro-osmosis of a substance into a tissue results from the migration of a solvent containing the substance as a result of the application of electromotive force to the substance.

The substance, in one embodiment, is a medicament. A "medicament" as used herein is any natural, homeopathic or synthesized material that may be applied to a biological substrate of choice. Thus, according to one embodiment, a medicament is a medicine, a healing or therapeutic substance, or a substance that promotes recovery from injury or ailment. "Medicament" may further be defined as a chemical or biological material that may be used or administered to a biological subject of choice (e.g. humans or animals) as an aid in diagnosis, treatment or prevention of disease or abnormal cosmetic condition, or relief of pain, or to control, diagnose or improve any physiological or pathological condition.

In a non-limiting example, the medicament may be comprised of a lotion applied to the skin of a human which contains a substance capable of imparting a beneficial effect. Alternatively, the medicament may take one of many forms and may be formulated, for example, as a liquid, gel, an ointment, a powder, a lotion, a foam, a solution, a cream, or any other known substance for application to a biological surface or tissue, depending on the nature of the medicament and procedure. In one embodiment, the medicament is present in an electroconductive gel used with the device.

In one example, the medicament may be comprised of a lotion or gel applied to the skin to enhance the blood flow of the capillaries and vessels of the skin. This increased blood flow via iontophoresis may be in addition to the vibrationally-induced blood flow increases discussed above. As such, the presently disclosed apparatus may be capable of providing increased blood flow in the capillaries and vessels of the skin through more than one method, the combination thereof provides a synergistic effect for the enhancement of blood flow therein. Use of iontophoresis and/or a medicament is optional, where the current is directed to producing electro-osmotic effects, but may also support iontophoresis The terms "substantially" or "generally" as used herein to refer to a shape is intended to include variations from the true shape that do not affect the overall function of the device. The term "about," as used herein, should generally be understood to refer to both numbers in a range of numerals. Moreover, all numerical ranges herein should be understood to include any number falling within the range. The terms "front," "back," "upper," "lower," "side" and/or other terms indicative of direction are used herein for convenience and to depict relational positions and/or directions between the parts of the embodiments. It will be appreciated that certain embodiments, or portions thereof, can also be oriented in other positions.

While illustrative embodiments are disclosed herein, it will be appreciated that numerous modifications and other embodiments can be devised by those of ordinary skill in the art. Features of the embodiments described herein can be combined, separated, interchanged, and/or rearranged to generate other embodiments. Therefore, it will be understood that the appended claims are intended to cover all such modifications and embodiments that come within the spirit and scope of the present disclosure.

What is claimed is:

1. A method for treating dermis and/or hypodermis on a body, the method comprising:
    providing at least a first electrode capable of placement at the surface of a to-be-treated skin region having a dermis and a hypodermis with fat globules causing skin dimpling and a second electrode capable of placement at another position on the body to be treated;
    applying between the electrodes a current pulse cycling between two values in a range from 0.500 mA to −0.500 mA, said current pulse appearing as a waveform that holds its peak value for at least one mS, wherein the current cycles between the two values at a cycling frequency in the range from 1 to 100 Hz and being sufficient in amplitude and duration to produce electro-osmotic wavefronts corresponding to the cycling frequency of the current pulse; and
    cycling the current between the two values to produce the electro-osmotic wavefronts in blood vessels in at least one of the dermis and hypodermis flow in which an electrical double layer formed is much smaller than the characteristic length scale of a channel of such blood vessels;
    wherein the current is selected to induce electro-osmotic flow at the cycling frequency, producing a vibratory action to increase blood in the skin region to be treated.

2. The method of claim 1 wherein the current pulse is applied with a cycling frequency in the range from 20 to 100 Hz.

3. The method of claim 2, wherein the current pulse is sufficient for the electro-osmotic wavefronts to produce the vibratory action in walls of the blood vessels with a frequency corresponding to the cycling frequency.

4. The method of claim 1 wherein applying a current pulse between the electrodes comprises applying a current pulse in the range from 0.100 to 5.0 milliamps measured on a root-mean-square basis.

5. The method of claim 1 wherein placing the first and second electrodes comprises placing them adjacent but separated from each other on the to-be-treated skin region.

6. The method of claim 1 further comprising applying a conductive gel between the skin region to-be-treated and the first electrode.

7. The method of claim 1 further comprising applying a conductive gel between the skin region to-be-treated and the first electrode, said conductive gel comprising an active chemically configured to be driven into the skin region by iontophoresis from the applied current.

8. The method of claim 1 wherein the cycling frequency is chosen in the range from about 35 to about 55 Hz or about 40 to about 50 Hz.

9. The method of claim 1 wherein the fat globules are distending and the to-be-treated skin region exhibits a cellulite condition, and further comprising selecting the current to increase the blood flow through the blood vessels to help reverse excess accumulation of lipids in the fat globules.

10. The method of claim 1 wherein the current has a DC component, such that the waveform consists of DC square wave pulses.

11. The method of claim 1 wherein the current pulse has a waveform chosen from a square, a sawtooth, a triangular, and a trapezoidal waveform or combinations thereof.

12. The method of claim 1 wherein the current pulse is sufficient for the electro-osmotic wavefronts to induce eNOS production in the skin region.

13. The method of claim 1 wherein wavefronts are produced in blood vessels in both of the dermis and hypodermis.

* * * * *